(12) United States Patent
Oberski et al.

(10) Patent No.: US 7,170,075 B2
(45) Date of Patent: Jan. 30, 2007

(54) INSPECTION TOOL WITH A 3D POINT SENSOR TO DEVELOP A FOCUS MAP

(75) Inventors: Norman L. Oberski, Chaska, MN (US); Mark R. Harless, Plymouth, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 133 days.

(21) Appl. No.: 10/622,848

(22) Filed: Jul. 18, 2003

(65) Prior Publication Data

US 2004/0056173 A1 Mar. 25, 2004

Related U.S. Application Data

(60) Provisional application No. 60/397,355, filed on Jul. 18, 2002.

(51) Int. Cl.
*G01N 21/84* (2006.01)
*G01N 21/88* (2006.01)
*G01N 21/86* (2006.01)
*G01B 11/06* (2006.01)

(52) U.S. Cl. ............................ 250/559.27; 250/559.19; 250/559.22; 356/630; 382/145

(58) Field of Classification Search ............ 250/559.19, 250/559.27, 559.22; 356/630; 382/145, 382/147, 149, 151
See application file for complete search history.

(56) References Cited

U.S. PATENT DOCUMENTS

| | | | |
|---|---|---|---|
| 5,780,866 A * | 7/1998 | Yamamura et al. | 250/559.22 |
| 6,107,637 A * | 8/2000 | Watanabe et al. | 250/559.3 |
| 6,172,365 B1 * | 1/2001 | Hiroi et al. | 250/310 |
| 6,208,407 B1 * | 3/2001 | Loopstra | 355/53 |
| 6,324,298 B1 * | 11/2001 | O'Dell et al. | 382/149 |
| 6,597,006 B1 * | 7/2003 | McCord et al. | 250/559.19 |
| 6,611,344 B1 * | 8/2003 | Chuang et al. | 356/601 |
| 6,674,510 B1 * | 1/2004 | Jasper et al. | 355/55 |
| 6,876,438 B2 * | 4/2005 | Tokita | 355/72 |
| 2002/0100872 A1 * | 8/2002 | Hiroi et al. | 250/310 |
| 2003/0053676 A1 * | 3/2003 | Shimoda et al. | 382/145 |
| 2004/0021877 A1 * | 2/2004 | Clark | 356/630 |
| 2004/0031779 A1 | 2/2004 | Cahill et al. | |
| 2004/0080742 A1 * | 4/2004 | Mizuo et al. | 356/237.4 |
| 2004/0130691 A1 * | 7/2004 | Boonman et al. | 355/53 |

* cited by examiner

*Primary Examiner*—Stephone B. Allen
*Assistant Examiner*—Davienne Monbleau
(74) *Attorney, Agent, or Firm*—Dicke, Billig & Czaja, PLLC

(57) ABSTRACT

An inspection system, and process for use thereof, for inspecting semiconductors or like substrates. The inspection system includes an inspection device and an auxiliary sensor apart from the inspection device. The auxiliary sensor is used to collect height data and generate a map of a semiconductor or like substrate to aids in focusing the inspection device.

21 Claims, 1 Drawing Sheet

INSPECTION TOOL WITH A 3D POINT SENSOR TO DEVELOP A FOCUS MAP

REFERENCE TO RELATED APPLICATION

This application claims the benefit of U.S. Provisional Application No. 60/397,355, filed Jul. 18, 2002.

BACKGROUND OF THE INVENTION

1. Technical Field

The present invention relates to a system, and process for use thereof, for inspecting wafers and other semiconductor or microelectronic substrates.

2. Background Information

Over the past several decades, microelectronics and semiconductors have exponentially grown in use and popularity. Microelectronics and semiconductors have in effect revolutionized society by introducing computers, electronic advances, and generally revolutionizing many previously difficult, expensive and/or time consuming mechanical processes into simplistic and quick electronic processes. This boom has been fueled by an insatiable desire by business and individuals for computers and electronics, and more particularly, faster, more advanced computers and electronics whether it be on an assembly line, on test equipment in a lab, on the personal computer at one's desk, or in the home via electronics and toys.

The manufacturers of microelectronics and semiconductors have made vast improvements in end product quality, speed and performance as well as in manufacturing process quality, speed and performance. However, there continues to be demand for faster, more reliable and higher performing semiconductors.

One process that has evolved over the past decade plus is the microelectronic and semiconductor inspection process. The merit in inspecting microelectronics and semiconductors throughout the manufacturing process is obvious in that bad wafers may be removed at the various steps rather than processed to completion only to find out a defect exists either by end inspection or by failure during use. In the beginning, wafers and like substrates were manually inspected, such as by humans using microscopes. As the process has evolved, many different systems, devices, apparatus, and methods have been developed to automate this process, such as the method developed by August Technology and disclosed in U.S. Pat. No. 6,324,298, which is incorporated herein by reference. Many of these automated inspection systems, devices, apparatus, and methods focus on two dimensional inspection, that is inspection of wafers or substrates that are substantially or mostly planar in nature.

One of the most important parameters that need to be controlled for any optical wafer inspection system such as that described above is keeping the focus of the inspection device, such as an optical sensor or camera, within the depth of field of the lens used. Typically this is done in one to two ways: 1) adding a focus sensor into the optical path and measuring the quality of the focus at all times whereby the feedback from this sensor is sent to a motion controller, which in turn adjusts the focus mechanism to keep the system in focus, or 2) moving the camera through a range of heights and taking pictures of the wafer at each height, and then using an image processing algorithm to determine the height of best focus. Each of these techniques has it own set of problems. One problem with the first technique is that at higher inspection stage velocities (>100 mm/sec), these types of sensors do not have the capability to guarantee that the image stays in focus because of rapid motion of the inspection stage during the inspection process. The problems with the second technique include time and video focus. As to time, it just takes too long to use video focus on an array of points as it typically takes 1–2 seconds per focus point. As to video focus, in many steps during wafer processing there is very little pattern on the wafer, which makes a video focusing algorithm impossible to implement because the system cannot get any information to use to determine the best focus height.

SUMMARY OF THE INVENTION

The inspecting of semiconductors or like substrates by the present invention solves these problems by including an auxiliary sensor for mapping the sample height.

BRIEF DESCRIPTION OF THE DRAWINGS

Preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE PREFERRED EMBODIMENT

Figure 1:
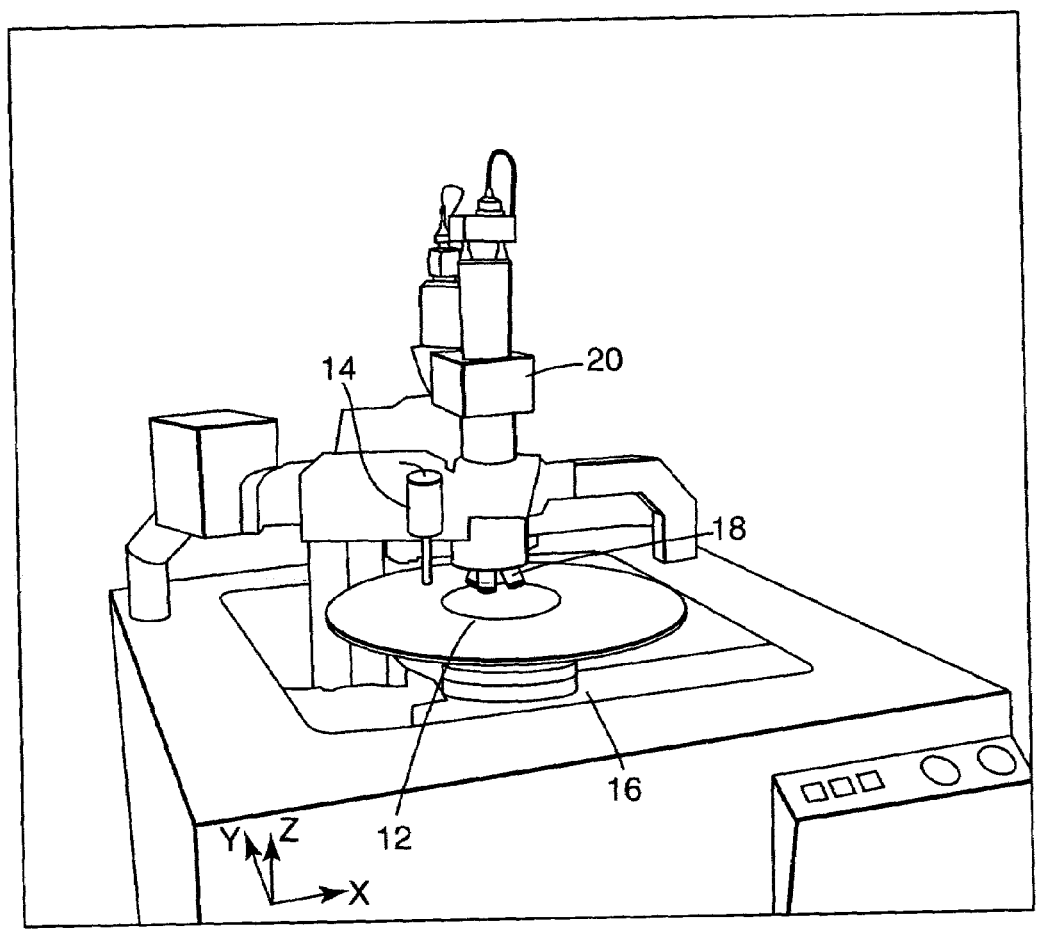
FIG. 1 is a perspective view of an inspection system.

The inspection system of the present invention is illustrated in FIG. 1. The inspection system includes an optical sensor or camera 20, one or more selectable focusing mechanisms 18, such as objectives or lenses, an auxiliary sensor 14, and an inspection platform 12 coupled to a wafer alignment device 16 for moving the platform 12 relative to the camera 20.

The inspection platform 12 is a rotary stage that is equipped with a universal interface platform with vacuum, all of which provides a flexible interface for wafer and die package fixturing. It is defined such that it quickly mounts and inspects whole wafers, sawn wafers on film frame, die in gel pak, die in waffle-pak, MCM, JEDEC trays, Auer boats, and other wafer and die package arrangements and configurations.

The wafer alignment device 16, which aligns each and every wafer at the same x, y, z, and θ location, is a precision system of rotary motors, ball screws, direct or belt driven motors, worm or other gears, actuators, hydraulics, push rods, vacuums, or other mechanical or electrical equipment for moving the rotary stage either linearly or angularly to a precise desired location.

The focusing mechanism 18 is an optical imaging mechanism with multiple optics therein for using different inspection resolutions. A motorized microscopic turret allows for selecting of the imaging optics from the multiple choices. For instance, a number of optics, such as three or five optics, may be supplied and typical choices include 1.25×, 2.5×, 5×, 10×, 20×, 50×and 100× objectives. The motorized microscopic turret and discrete objectives provide the means to select the optical magnification.

The camera system 20 or other visual inspection device is for visual inspection of wafers or die. The camera system may be any type of camera capable of high resolution inspection. An example of one part of such a camera system is a 3-CCD inspection camera used to capture die or other images during defect analysis.

The inspection system inspects semiconductors or like substrates by keeping the focus of the optical sensor or camera 20 within the depth of field of the lens 18 used. The system specifically uses the process of making a separate pass over the wafer surface using an auxiliary sensor 14, such as a 3D point sensor, before the inspection of the wafer situated on inspection stage 12 begins. At precise points on the wafer, height measurements are taken by the 3D point sensor, with or without stopping. The 3D point sensor can take hundreds or thousands of samples per second, and thus is very fast at collecting wafer focus samples. These wafer focus samples are then put in any pattern on the wafer that the user desires. The pattern may comprise a single point, a random set of points, a specified set of points, or a fixed 2D grid of points. Using the wafer focus samples and a calibration process for each objective 18, the x, y, z offset (position over the wafer in the horizontal x-y plane and the height z above the wafer) for each objective 18 and the focus of the sensor 20 is known. Once these points are collected and transformed into objective coordinates, interpolation techniques are used to calculate the exact height for each picture it is desirable to collect for the entire wafer inspection process. Once these points are fed into a path planning system, all of these points are moved through with speeds much higher than those allowed by the first technique (>100 mm/sec).

In addition, using a high accuracy 3D point sensor having an equal or better depth of field than the highest objective eliminates the need for focusing during inspection of a wafer at high magnification.

In one embodiment, the 3D point sensor is used to measure the difference in height of features on the wafer. The features may include gold or solder interconnects, etc.

In one embodiment, a calibrator is used to find the offset between the 3D point sensor and an inspection lens or matrix of lenses.

Coverage using a point sensor is also improved. Whereas video focus techniques rely on image contrast, different points of point sensor 14 can be swapped in for particular needs. For instance, a confocal point sensor can be used for measuring the height of transparent materials or materials with uniform intensities.

Accordingly, the invention as described above and understood by one of skill in the art is simplified, provides an effective, safe, inexpensive, and efficient device, system and process, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. An inspection system comprising:
    a primary optical inspection device including a focusing mechanism for focusing the primary optical inspection device over a predetermined optical field of view to optically inspect a sample; and
    an auxiliary sensor apart from the focusing mechanism, the auxiliary sensor for mapping a sample height by obtaining height data for at least one point on the sample, wherein the at least one point is offset from the field of view of the primary optical inspection device.

2. The inspection system of claim 1, wherein the height data is used to position the inspection device in focus during an inspection of the sample.

3. The inspection system of claim 1, wherein the height data is used in an interpolation to calculate an exact height of each picture needed for the inspection of the sample by the inspection device.

4. The inspection system of claim 1, wherein mapping the sample height is performed as a separate operation before inspection of the sample by the inspection device occurs.

5. The inspection system of claim 1, wherein the process of mapping the sample height is performed concurrent with inspection of the sample by the inspection device.

6. The inspection system of claim 1, wherein the auxiliary sensor is used to measure a difference in height of features on the sample.

7. The inspection system of claim 6, wherein the features measured comprise gold or solder interconnects.

8. The inspection system of claim 1, wherein the height data comprises a pattern comprising a single point, a random set of points, a specified set of points, or a fixed 2D grid of points.

9. The inspection system of claim 1, further comprising:
    a calibrator for finding the offset between the auxiliary sensor and an inspection lens or matrix of lenses.

10. The inspection system of claim 1, wherein the auxiliary sensor comprises a 3D point sensor.

11. An inspection system comprising:
    a camera for inspecting a wafer surface; and
    a 3D point sensor apart from the camera for generating height data for a plurality of points on the wafer surface; and
    a wafer mapping module for using the height data to generate a three-dimensional height map of the wafer surface prior to an inspection of the wafer surface;
    wherein the three-dimensional height map is used for setting the focus of the camera during the inspection.

12. The inspection system of claim 11, further comprising:
    an inspection platform for holding the wafer while the wafer is inspected.

13. The inspection system of claim 12, further comprising:
    a wafer alignment device coupled to the inspection platform for moving the inspection platform relative to the camera.

14. The inspection system of claim 11, further comprising:
    an objective for use with the camera for inspecting the wafer.

15. The inspection system of claim 14, wherein the 3D point sensor has an equal or better depth of field than the objective to eliminate the need for focusing during inspection of the wafer.

16. The inspection system of claim 11, further comprising:
    a plurality of selectable objectives for selective use with the camera for inspecting the wafer.

17. The inspection system of claim 11, wherein the 3D point sensor is a confocal point sensor.

18. A method for inspecting a wafer comprising:
providing an inspection sensor for inspecting a surface of the wafer in an optical field of view of the inspection sensor;
providing an auxiliary sensor apart from the inspection sensor for obtaining height data of the surface of the wafer;
obtaining a pattern of height data of the surface of the wafer using the auxiliary sensor, wherein the pattern of height data is obtained outside the optical field of view of the inspection sensor; and
inspecting the surface of the wafer by focusing the inspection sensor using the height data.

19. The method of claim 18, wherein the inspection sensor comprises a camera.

20. The method of claim 19, wherein inspecting the surface of the wafer by focusing the inspection sensor using the height data comprises interpolating the height data to determine heights at which to take pictures of the wafer.

21. The method of claim 18, wherein the auxiliary sensor comprises a 3D point sensor.

* * * * *

UNITED STATES PATENT AND TRADEMARK OFFICE
CERTIFICATE OF CORRECTION

PATENT NO.        : 7,170,075 B2
APPLICATION NO. : 10/622848
DATED             : January 30, 2007
INVENTOR(S)       : Norman Oberski et al.

It is certified that error appears in the above-identified patent and that said Letters Patent is hereby corrected as shown below:

In the Issued Patent, the Sheet Number is not provided for the sole figure. Please insert --Sheet 1 of 1--.

Column 2, line 59, delete "50xand" and insert in place thereof --50x and--.

Signed and Sealed this

Tenth Day of April, 2007

JON W. DUDAS
*Director of the United States Patent and Trademark Office*